United States Patent [19]
Sauer

[11] Patent Number: 5,674,213
[45] Date of Patent: Oct. 7, 1997

[54] ABSORBENT ARTICLE HAVING CONTAINMENT FLAPS WITH RECEIVING RESERVOIRS

[75] Inventor: Barbara Oakley Sauer, Fremont, Wis.

[73] Assignee: Kimberly Clark Corporation, Neenah, Wis.

[21] Appl. No.: 550,431

[22] Filed: Oct. 30, 1995

[51] Int. Cl.$^6$ .................................................. A61F 13/15
[52] U.S. Cl. .................... 604/385.1; 604/378; 604/385.2
[58] Field of Search ................................ 604/358, 378, 604/383, 385.1, 385.2, 373

[56] References Cited

U.S. PATENT DOCUMENTS

| | | | |
|---|---|---|---|
| Re. 33,106 | 11/1989 | Beckestrom | 604/385.2 |
| 4,490,148 | 12/1984 | Beckestrom | 604/385 |
| 4,662,877 | 5/1987 | Williams | 604/385 A |
| 4,681,579 | 7/1987 | Toussaint et al. | 604/385 R |
| 4,695,278 | 9/1987 | Lawson | 604/385 A |
| 4,704,116 | 11/1987 | Enloe | 604/385 A |
| 4,738,677 | 4/1988 | Foreman | 604/385 R |
| 4,743,246 | 5/1988 | Lawson | 604/385 A |
| 4,795,454 | 1/1989 | Dragoo | 604/385.2 |
| 4,808,177 | 2/1989 | DesMerais et al. | 604/385.2 |
| 4,808,178 | 2/1989 | Aziz et al. | 604/385.2 |
| 4,816,025 | 3/1989 | Foreman | 604/385.2 |
| 4,822,435 | 4/1989 | Igaue et al. | 156/164 |
| 4,834,740 | 5/1989 | Suzuki et al. | 604/385.2 |
| 4,846,823 | 7/1989 | Enloe | 604/385.2 |
| 4,883,482 | 11/1989 | Gandrez et al. | 604/385.2 |
| 4,892,536 | 1/1990 | DesMarais et al. | 604/385.2 |
| 4,900,384 | 2/1990 | Sanders et al. | 156/204 |
| 4,904,251 | 2/1990 | Igaue et al. | 604/385.2 |
| 4,909,803 | 3/1990 | Aziz et al. | 604/385.2 |
| 4,938,755 | 7/1990 | Foreman | 604/385.2 |
| 4,990,147 | 2/1991 | Freeland | 604/385.2 |
| 5,021,051 | 6/1991 | Hiuke | 604/385.2 |
| 5,026,364 | 6/1991 | Robertson | 604/385.1 |
| 5,032,120 | 7/1991 | Freeland et al. | 604/385.2 |
| 5,061,261 | 10/1991 | Suzuki et al. | 604/385.2 |
| 5,064,489 | 11/1991 | Ujimoto et al. | 156/164 |
| 5,085,654 | 2/1992 | Buell | 604/385.1 |
| 5,114,420 | 5/1992 | Igaue et al. | 604/385.2 |
| 5,167,653 | 12/1992 | Igaue et al. | 604/385.2 |
| 5,190,606 | 3/1993 | Merkatoris et al. | 156/164 |
| 5,207,662 | 5/1993 | James | 604/385.2 |
| 5,224,941 | 7/1993 | Simmons | 604/385.2 |
| 5,236,428 | 8/1993 | Zajaczkowski | 604/385.2 |
| 5,246,431 | 9/1993 | Minetola et al. | 604/385.2 |
| 5,246,432 | 9/1993 | Suzuki et al. | 604/385.2 |
| 5,269,775 | 12/1993 | Freeland et al. | 604/385.2 |
| 5,275,590 | 1/1994 | Huffman et al. | 604/385.2 |
| 5,292,316 | 3/1994 | Suzuki | 604/385.2 |
| 5,304,159 | 4/1994 | Tanji et al. | 604/385.2 |
| 5,304,160 | 4/1994 | Igaue et al. | 604/385.2 |

FOREIGN PATENT DOCUMENTS

| | | | |
|---|---|---|---|
| 2699812 | 7/1994 | France | 604/385.1 |
| 2707159 | 1/1995 | France | 604/385.1 |
| 3218751 | 9/1991 | Japan | 604/385.1 |
| 4152947 | 5/1992 | Japan | 604/385.1 |
| 3002647 | 2/1993 | WIPO | 604/385.2 |

*Primary Examiner*—Mark O. Polutta
*Attorney, Agent, or Firm*—Jeffrey B. Curtin; Thomas D. Wilhelm; Brian R. Tumm

[57] ABSTRACT

An absorbent article includes an absorbent core located between a bodyside liner and an outer cover. A containment flap is joined to the bodyside liner. A reservoir wall attaches to the containment flap and a base structure comprising, in combination, the bodyside liner and an outer cover. Passageways in the containment flaps allow exudates to flow from the region between the flaps and into a reservoir defined outwardly from the containment flap. In one embodiment, a surface near the outer edge of the reservoir wall is attached to the bodyside liner. In another embodiment, the reservoir wall attaches to the outer cover of the absorbent article. In yet another embodiment, the reservoir wall attaches to the containment flap, first near a distal edge thereof, and secondly near the base of the containment flap.

30 Claims, 3 Drawing Sheets

ABSORBENT ARTICLE HAVING CONTAINMENT FLAPS WITH RECEIVING RESERVOIRS

BACKGROUND OF THE INVENTION

1. Technical Field

The present invention relates to an absorbent article for receiving body exudates. Such absorbent articles may have containment flaps for impeding or containing spread or flow of the body exudates.

2. Description of the Related Art

Absorbent articles such as infant diapers, training pants, adult incontinence products, and the like are well known. Such articles have achieved a wide acceptance due to their ability to receive and absorb body exudates. In order to move bowel movements and other exudates away from the user's body, the prior art has considered utilizing an aperture in the center of the absorbent article.

For example, U.S. Pat. No. 4,892,536 to DesMarais et al. discloses a diaper with a large passageway in the center section of the bodyside liner to facilitate movement of solid and semi-solid waste materials away from the user's body. This arrangement was supposed to reduce contact of the waste with the skin of the wearer.

Freeland, U.S. Pat. No. 4,990,147 and Freeland et al., U.S. Pat. No. 5,269,775 are other patents that disclose similar attempts to prevent solid waste materials from contacting a wearer of a diaper.

The patents listed above all attempt to place the solid waste in direct contact with the absorbent core through a relatively large opening centrally located in the bodyside liner. Accordingly, the solid waste occupies a reservoir, centrally located in the absorbent article, between the bodyside liner and the absorbent core. There is no teaching of modifying any containment flaps to provide a path or direction for exudates to travel transversely across the length or width of the absorbent article to a receiving reservoir at or adjacent the outer perimeter of the absorbent article. Further, the aperture location shown in the above patents may not readily collect an overflow of urine. The sudden presence of a large quantity of urine was not addressed by these patents.

SUMMARY OF THE INVENTION

In order to improve the leakage protection of a diaper, the present invention modifies one or more containment flaps of an absorbent article by providing passageways or openings, preferably near the base of the flaps that lead into a receiving reservoir, at or adjacent the outer perimeter of the absorbent article. The reservoir receives urine, fecal material or other exudates which travel through the openings e.g. as pressure builds from a pool against the flap. The openings in the containment flaps thus prevent the exudates from leaking over or around the containment flaps by providing an alternative path for releasing the pressure against the containment flaps.

In one aspect, the present invention resides in an absorbent article having a front portion, a rear portion and a crotch portion connecting the front and rear portions, the crotch portion having opposite longitudinal side portions. The absorbent article includes a base structure, the base structure comprising, in combination, a liquid-permeable bodyside liner and an outer cover. An absorbent core is located between the bodyside liner and the outer cover. A containment flap is joined to the bodyside liner and includes at least one passageway formed through the containment flap. A reservoir wall is attached to the flap and the base structure to form a reservoir for exudates.

Another embodiment of the invention resides in an absorbent article having a front portion, a rear portion and a crotch portion connecting the front and rear portions, the crotch portion having opposite longitudinal side portions. The absorbent article includes a base structure, the base structure comprising, in combination, a liquid-permeable bodyside liner and an outer cover. An absorbent core is located between the bodyside liner and the outer cover. First and second longitudinally extending leg cuffs are located in the crotch portion at oppositely disposed longitudinal side portions thereof. The absorbent article also includes a pair of containment flaps containing at least one passageway and extending longitudinally from the front portion to the rear portion of the article, the flaps being joined to the bodyside liner. Respective first and second reservoir walls are attached to a respective one of the containment flaps at corresponding first loci. A second locus of each reservoir wall is attached to the base structure at a position disposed outwardly from the respective containment flap and inwardly from the outer edge of the bodyside liner.

In another embodiment, the reservoir wall may be attached to the outer cover outwardly of the flaps.

In yet another embodiment, the reservoir wall may be attached at the top distal end of the containment flap and at the lower base of the containment flap. This arrangement forms the reservoir with the containment flap and reservoir wall only.

The passageways may comprise slits, apertures of various shapes, as well as breaks in the seams joining the respective containment flaps to the bodyside liner. The apertures preferably have an open area of no more than about 7 square centimeters for each flap, and preferably have cross-sectional areas corresponding to diameters from 5 to 25 millimeters. At least one passageway, and preferably at least three passageways are contemplated for each containment flap.

Further, the passageways may be formed by cuts in the containment flaps, the cuts being serpentine in configuration and forming serpentine edges, and being effected before attachment to the bodyside liner. The serpentine edges provide lobes and open or cut-out spaces between the respective lobes. The containment flaps are not attached to the liner at these spaces when the distal ends of the lobes are bonded or otherwise attached to the bodyside liner at intermittent locations. These spaces then comprise the passageways referred to earlier.

Further, the passageways may be formed by cuts in the containment flaps, the cuts being zig-zag in configuration and forming zig-zag edges, and being effected before attachment to the bodyside liner. The zig-zag edges provide teeth and open or cut-out spaces between the respective teeth. The containment flaps are not attached to the liner at these spaces when the distal ends of the teeth are bonded or otherwise attached to the bodyside liner. These spaces then comprise the passageways referred to earlier.

DETAILED DESCRIPTION OF THE PREFERRED EMBODIMENT

The present invention relates to absorbent articles designed to absorb body exudates. While the preferred embodiments of the present invention will be described in terms of a disposable diaper adapted to be worn by infants and toddlers about the lower torso, the present invention is equally applicable to other absorbent articles such as adult incontinent briefs, training pants and the like.

Figure 1:
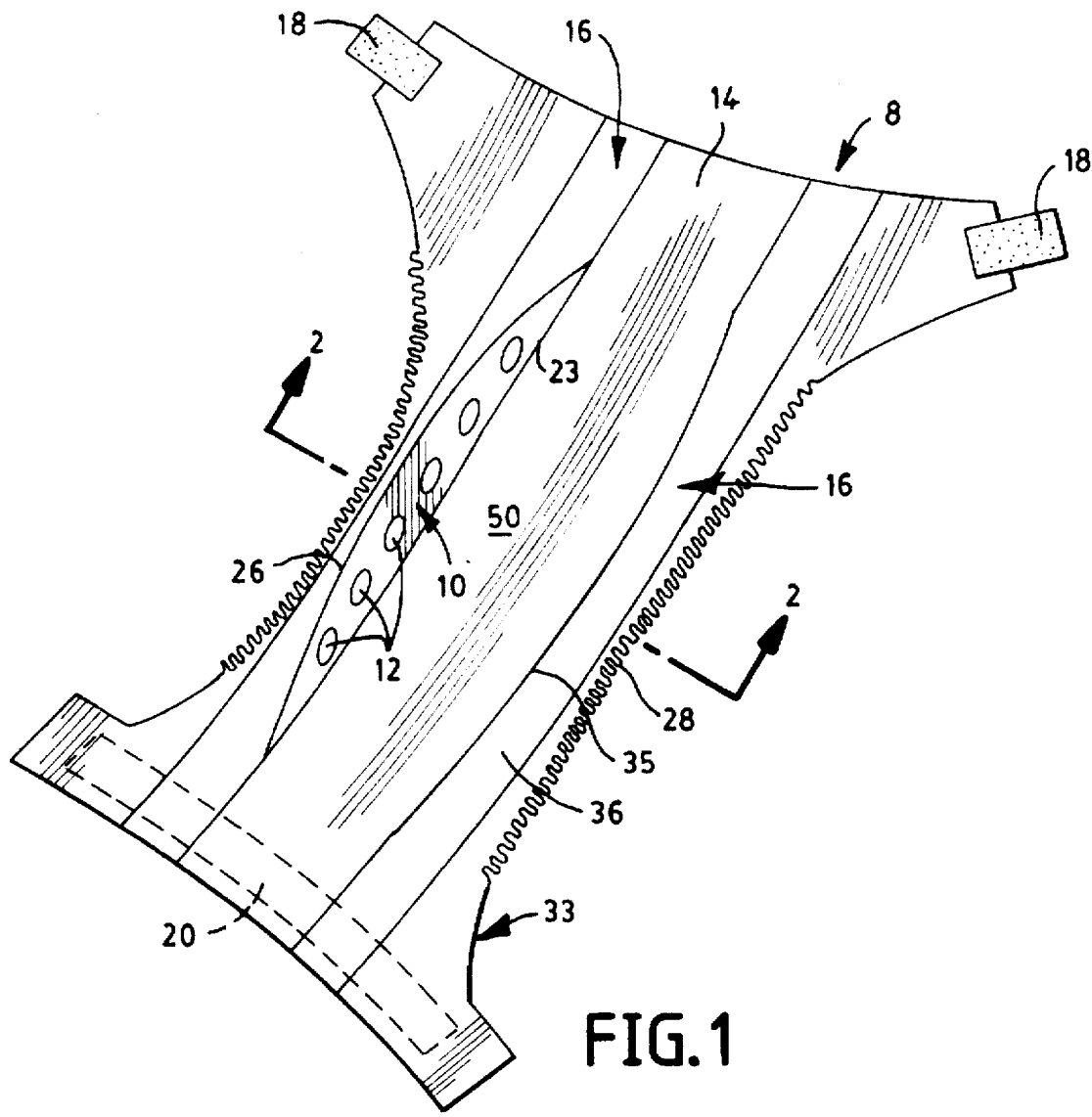
FIG. 1 illustrates an absorbent article according to the present invention.

The present invention can best be understood by a reference to the drawings in which like numerals represent like elements. FIG. 1 illustrates a diaper 8 suitable for use in the present invention. The diaper 8 of FIG. 1 shows the containment flaps 10, the passageways 12, the bodyside liner 14 and the reservoir wall 16. FIG. 1 also shows attachment means, such as hook and loop fasteners 18, 20, for securing the diaper upon a child. The first fastener 18 comprises a mechanical fastener such as the hook of a hook and loop fastening system mounted on the outer cover 22. The second fastener 20 then comprises a corresponding loop material attached to the outer cover 22 and adapted to releasably engage with the hook material of the first fastener 18. Further, other well known fastening means may be used to support the diaper 8 upon a person. Also, as shown in FIG. 1, the passageways 12 are preferably located at or adjacent the base 23 of the containment flaps 10.

Figure 2:
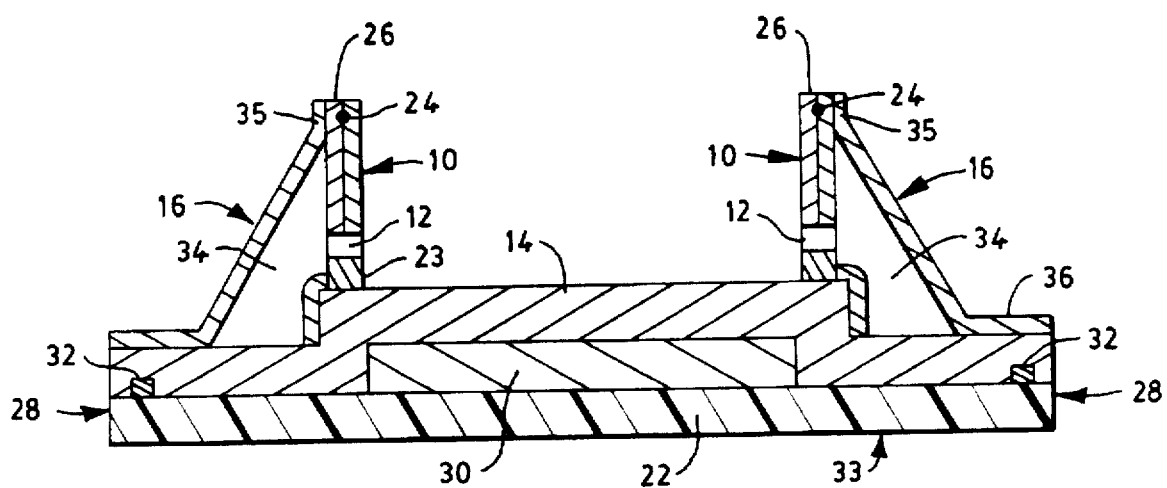
FIG. 2 illustrates a cross-sectional view taken at 2—2 in FIG. 1 of a diaper with the reservoir wall attached to the containment flap and the bodyside liner.

The containment flaps 10 shown in FIGS. 1 and 2 include elasticized material 24 to shape and position the flap. The flap material may be somewhat permeable. The containment flaps 10 may be joined to the bodyside liner by heat sealing, sonic bonding, adhesive bonding or the like. Adhesive bonding includes the use of glue lines, glue dots or other arrangements.

Figure 5:
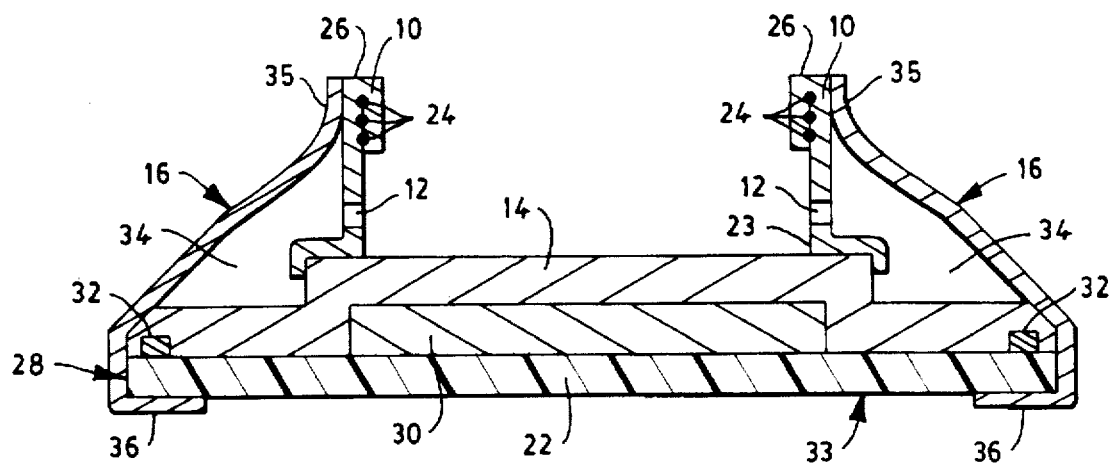
FIG. 5 is a cross-sectional view of another diaper with the reservoir wall attached to the containment flap and the outer cover.
Figure 6:
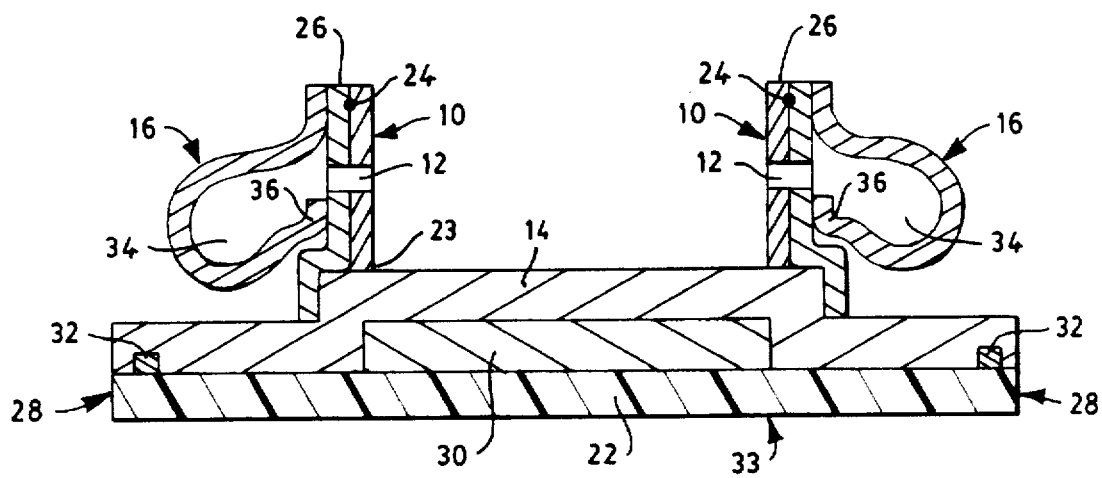
FIG. 6 is a cross-sectional view of yet another diaper with the reservoir wall attached only to the containment flap.

Containment flaps 10 may include flap elastics 24 as shown in FIG. 2. These flap elastics may suitably comprise one or more individual strands of elastomeric material. For example, a plurality of elastic strands may be configured in a spatially separated, generally parallel arrangement. The elastic strands can be distributed over the full width of the flap and formed of a rubber material. The elastic strands may also be placed in an intermediate position or fold of the containment flap 10 in a lengthwise direction. The elastic strands may run the entire length of the containment flap 10 or only a portion of the length of the containment flap near the crotch of the diaper 8. A suitable elastic strand may, for example, be composed of a 470 decitex LYCRA® elastomer, 620 decitex LYCRA® elastomer or other elastomers with suitable characteristics. Flap elastics 24 are preferably integrated into containment flaps 10 at least adjacent the distal edge 26 of the respective containment flap 10 and remote from bodyside liner 14 in a stretched condition such that the contraction of the elastic components thereof gathers and shortens the distal edge 26 of the containment flap 10 from the fully extended condition. As a result, the distal edge 26 of the containment flap 10 tends to position itself in a spaced relation away from the bodyside liner 14 toward a generally upright and approximately perpendicular configuration in especially the crotch portion of the diaper as shown in FIGS. 2, 5 and 6.

Leg cuffs 28 are suitably formed by portions of the outer cover 22 and/or the bodyside liner 14, which extend transversely beyond the longitudinal sides of the absorbent core 30. The leg cuffs 28 may also be formed from separate materials which are attached to the outer cover 22 and/or the bodyside liner 14. Leg cuffs 28 include leg elastics 32. Materials suitable for forming leg elastics 32 include strands or ribbons of a polymeric, elastomeric material which are adhered to the diaper 8 at the leg cuff 28 while in a stretched position, or which are attached to the diaper 8 while the diaper is pleated, such that elastic constrictive forces are imparted to the leg cuff 28. Further, the leg elastics 32 shown in FIGS. 2 and 5 may be made of a material similar or identical to the flap elastics 24.

The containment flaps 10 may be constructed of a material which is the same as, or different than the material comprising bodyside liner 14. Alternatively, the containment flaps 10 may also be made from a material which is the same as the material of outer cover 22. The containment flaps 10 are preferably liquid impervious. The containment flap 10 may be formed from a polymeric film material or from e.g. a nonwoven material which is substantially liquid impervious. The containment flaps 10 may be formed by a single or multiple layer of material with appropriate elastics secured thereto as shown in FIG. 5. FIGS. 2, 5 and 6 show the presence of the elastics 24 in the containment flap. Other arrangements are also contemplated. For example, the elastics may be placed at multiple locations on the containment flap 10.

A suitable bodyside liner 14 may be manufactured from a wide selection of web materials, such as porous foams, reticulated foams, apertured plastic films or natural fibers. For example, the bodyside liner 14 may comprise wood or cotton fibers. Other possible materials are synthetic fibers, such as polyester or polypropylene fibers, or a combination of natural and synthetic fibers. Bodyside liner 14 is suitably utilized to help isolate the liquids held in the absorbent core 30 from the wearer's skin.

Various woven and nonwoven fabrics may be used for bodyside liner 14. For example, bodyside liner 14 may be composed of a meltblown or spunbonded web of polyolefin fibers. The bodyside liner may also comprise a carded and/or bonded web composed of natural and/or synthetic fibers. The bodyside liner may also be composed of a substantially hydrophobic material wherein the hydrophobic material is treated with a surfactant or otherwise processed to impart a desired level of wettability and hydrophilicity. In a particular embodiment of the present invention, the bodyside liner 14 may comprise a nonwoven, spunbond, polypropylene fabric composed of about 2.8–3.2 denier fibers formed into a web having a basis weight of about 22 grams per square meter and a density of about 0.06 grams per cubic centimeter. The fabric is then surface treated with about 0.28 weight percent of a surfactant. The bodyside liner 14 may comprise a multiplicity of components or layers which correspond to any of the materials disclosed herein, as well as others known in the art.

It is generally preferred that the outer cover 22 of the diaper 8 be formed from a material which is substantially impermeable to liquids. A typical outer cover 22 may be manufactured from a thin plastic film or other flexible liquid-impermeable material. For example, the outer cover 22 may be formed from a polyethylene film having a thickness of from about 0.012 millimeters to about 0.051 millimeters. If the outer cover 22 should have a more clothlike feeling, it may comprise a polyethylene film laminated to a surface of a nonwoven web, such as a spunbond web of polyolefin fibers. For example, a polyethylene film having a thickness of about 0.015 millimeters may have thermally laminated thereto a spunbond web of polyolefin fibers having a thickness from 1.5 to 2.5 denier per filament, which nonwoven web has a basis weight of about 24 grams per square meter. Further, the outer cover 22 may be formed of a woven or nonwoven fibrous web which has been totally or partially constructed or treated to impart a desired level of liquid impermeability to selected regions that are adjacent or proximate the absorbent core 30. Still further, the outer cover 22 may optionally be composed of a microporous material which permits vapors to escape from the absorbent core 30 while still preventing liquid exudates from passing through the outer cover 22. The outer cover 22 and bodyside liner 14, in combination form a base structure 33 for the diaper 8.

The absorbent core 30 suitably comprises a matrix of hydrophilic fibers, such as a web of cellulosic fluff, in combination with a high-absorbency material commonly known as superabsorbent material. In a particular embodiment, absorbent core 30 comprises a mixture of superabsorbent hydrogel-forming particles and wood pulp fluff. In place of the wood pulp fluff, one may use synthetic, polymeric, meltblown fibers or a combination of meltblown fibers and natural fibers. The superabsorbent material may be substantially homogeneously mixed with the hydrophilic fibers or may be otherwise combined into the absorbent core.

Alternatively, the absorbent core 30 may comprise a laminate of fibrous webs and superabsorbent material or other suitable means of maintaining a superabsorbent material in a localized area.

The absorbent core 30 may have any of a number of shapes. For example, the absorbent core may be rectangular, I-shaped or T-shaped. It is generally preferred that the absorbent core 30 be narrower in the crotch portion than the rear or front portion.

The high-absorbency material in the absorbent core 30 can be selected from natural, synthetic and modified natural polymers and materials. The high absorbency materials can be inorganic materials, such as silica gels, or organic compounds, such as crosslinked polymers. The term crosslinked refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

The top edges (See FIGS. 2 and 5) of the reservoir walls 16 are preferably attached to the containment flaps 10 at or near the distal edges 26 of the containment flaps 10 and away from the bodyside liner 14. The reservoir walls can be formed of materials similar to those contained in the outer cover 22. The reservoir walls 16 preferably are formed of an impermeable nonwoven material or film, and/or combination of the two. Examples of materials for the reservoir walls 16 include a polyethylene film having a thickness of about 0.012 millimeters or a polyethylene film thermally laminated to a spunbond web of polyolefin fibers. The reservoir walls 16 are also preferably attached to the base structure 33 outwardly from the containment flap 10 and toward the outer edge of the diaper 8 as shown in FIGS. 2 and 5. This arrangement forms a reservoir 34 to receive exudates.

At a first locus of attachment, a first surface of a reservoir wall 16, near an upper edge 35 thereof, is bonded or attached to a corresponding surface of the respective containment flap 10 near the distal edge 26. The lower edge 36 of the reservoir wall 16 is attached to the base structure 33 and/or containment flap 10 near base 23. For instance, a surface near a lower edge 36 of the reservoir wall 16 is attached to a corresponding surface of the base structure 33. Therefore, the reservoir wall 16 is attached to the containment flap 10 and base structure 33 to thereby form the reservoir 34.

This arrangement allows urine and/or fecal material and the like to travel through the passageway 12, including in response to pressure against the containment flap 10. The exudates are then received by the reservoir 34 formed between the reservoir wall 16, the containment flap 10, and optionally the base structure 33. In general, the exudates pass through the passageway 12 into reservoir 34 in preference to leaking past or over the containment flaps 10. The reservoir wall 16 may be attached to the containment flap 10 and base structure 33 by sewing, heat sealing, sonic bonding, adhesive bonding or the like.

The passageways 12 of a containment flap 10 are large enough that a runny bowel movement and/or urine may pass through, but small enough to avoid entrapment of body parts. The passageways 12 may comprise slits, apertures of various shapes, as well as interruptions in the joinder between the containment flap and the bodyside liner. The apertures of passageways 12 may have a total combined open area from 0.1 to 7 square centimeters for each containment flap 10. Preferably each aperture has an open area corresponding to a cross-sectional area of a diameter from about 5 to about 25 millimeters. Preferably each individual aperture is no greater than 0.5 square centimeters to avoid any possibility of penile strangulation. Slits may have a length from about 5 to about 25 millimeters. Preferably, the slits are less than 12 millimeters long to avoid any possibility of penile strangulation. In most instances, all of the apertures combined, have a total open area for both containment flaps 10 of no greater than 12 square centimeters. The passageways 12 may be intermittently spaced the entire length of the containment flap 10 as shown in FIG. 1 or may be confined to a targeted area. One such area would be along the back portion of the flap to collect exudates from bowel movements. A preferred area for the passageways 12 is along the base or bottom 23 of the containment flap 10 near the bodyside liner 14 as shown in FIG. 1.

While any number of passageways may be effective with respect to applicant's invention, preferably at least three passageways are present in each containment flap 10.

Figure 3:
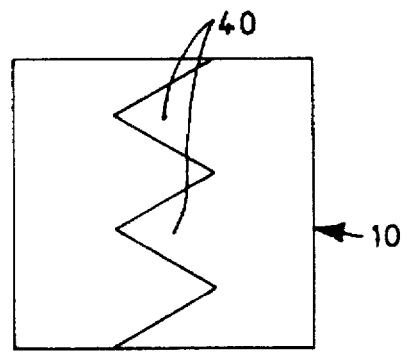
FIG. 3 illustrates a sheet of flap material with a zig-zag cut.
Figure 3A:
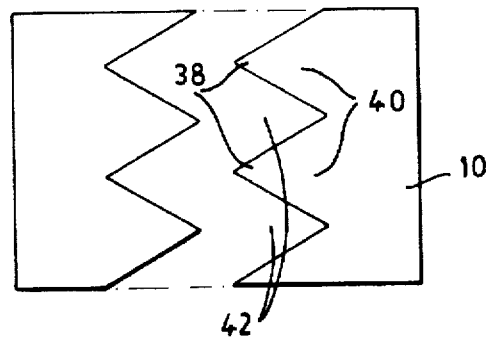
FIG. 3a illustrates a broken view of the sheet of flap material shown in FIG. 3.

The passageways 12 may be formed by cutting a single piece of material into two containment flaps 10 in a zig-zag manner as shown in FIGS. 3 and 3a. After the cut is completed, two containment flaps with zig-zag edges are created from one piece of material as shown in FIG. 3a. Then, the distal portions 38 of the teeth 40 formed by the zig-zag edges of each containment flap 10 are sewn, bonded, or otherwise attached, preferably longitudinally onto the bodyside liner 14 at intermittent locations. When the containment flaps 10 are attached, open spaces 42 between the teeth 40 are left unattached or unbonded. This arrangement forms passageways 12 from the spaces 42 between the teeth 40 of the containment flaps 10 and there is no waste of any piece of the material when forming passageways 12.

Figure 4:
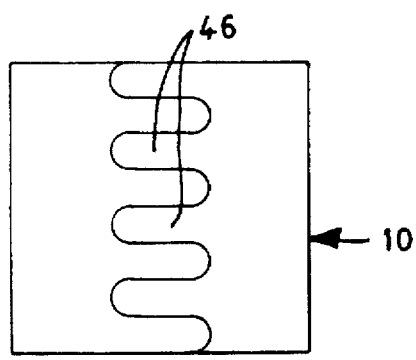
FIG. 4 illustrates a sheet of flap material with a serpentine cut.
Figure 4A:
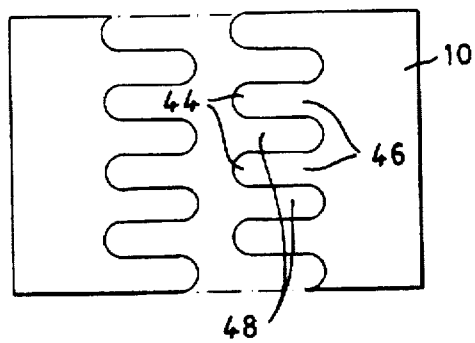
FIG. 4a illustrates a broken view of the sheet of flap material shown in FIG. 4.

Further, a serpentine pattern may be cut from a sheet of material as shown in FIGS. 4 and 4a. This sheet of material, when cut into two pieces, then becomes two containment flaps with serpentine edges. The distal portions 44 of the lengths or lobes 46 formed by the serpentine edges of each containment flap 10 are then sewn, bonded or otherwise attached, preferably longitudinally onto the bodyside liner 14 at intermittent locations. When the containment flaps 10 are attached, the open spaces 48 between the lobes 46 are left unattached or unbonded. This arrangement forms passageways 12 from the spaces 48 between the lobes 46 of the containment flaps 10. The second flap 10 created by edges of the serpentine cut is attached in a similar manner. Once again, the spaces 48 between the lobes 46 of the serpentine pattern then comprise passageways 12 which allow exudates to travel to the reservoir 34. Forming the flaps 10 in this manner ensures there is no waste of any piece of the material when forming passageways 12.

While a zig-zag pattern and a serpentine pattern have been illustrated, there are an infinite variety of other patterns which also may be utilized. The chief criteria for selecting a pattern is to provide the proper number of, and dimensions for, passageways 12.

The volume of the receiving reservoir 34 is controlled, at least in part, by the locus at which the upper edge 35 of the reservoir wall attached to the containment flap 10 and the locus at which the lower edge 36 of the reservoir wall 16 is attached to a surface of the base structure 33 or to the base 23 of containment flap 10. Attaching the lower edge 36 of the reservoir wall 16 to the outer cover 22 at a surface of the base structure 33 as shown in FIG. 5 contributes to an increased volume for the reservoir 34. In the illustrated embodiments, the longitudinal ends of the containment flaps 10 are also bonded or otherwise attached to the base structure 33. Similarly, the longitudinal ends of reservoir 34 are closed by securement of reservoir wall 16 to containment flap 10 along a line traversing from generally lower edge 36 to upper edge 35. This arrangement forms a reservoir 34 connected via the passageways 12 to the central portion 50 of the diaper 8 which may contain a sudden flow of exudates which could otherwise leak around or over the containment flaps 10. As shown in FIG. 1, central portion 50 extends for a length along the center of diaper 8. FIGS. 1 and 2 show bodyside liner 14 positioned between containment flaps 10 for contact with the skin of a user.

Further, as shown in FIG. 5, spacing the reservoir wall 16 outwardly from or beyond the leg elastics 32 maximizes the volume capacity of reservoir 34. This arrangement also allows exudates contained in reservoir 34 to pass through the bodyside liner 14 to reach the absorbent core 30. This allows more of the exudates to reach the absorbent core 30. In such instances where exudates travel first into reservoir 34 and thence to the core 30, reservoir 34 acts as a temporary holding locus, holding the exudates away from the user's body until liquid portions thereof are absorbed by core 30. This increases the efficiency and capability of the diaper 8 to operate effectively during a sudden release of exudates without leaking.

The spacing between containment flaps 10, across the central portion 50 of the diaper 8 can be varied in accordance with a variety of acceptable design parameters. As the containment flaps 10 are spaced closer together to minimize the stain area on the buttocks due to a bowel movement, the volume available between the flaps 10, absent the invention, to contain exudates is reduced. Absent the invention, as exudates fill the pocket in the central portion 50 of the diaper, the exudates begin to go over the flap, and/or up the back of the diaper. Therefore, the invention shown herein reduces the stain area and provides greater comfort to the wearer because an alternate path of low resistance is provided for movement of exudates through passageways 12 and away from the wearer's skin. With respect to urine, the same logic may be applied. A sudden flow of urine may be released more rapidly than the core 30 can absorb it. The excess urine can pass through passageway 12 to the reservoir 34 and be held there until it is absorbed by the absorbent core 30. Once in the reservoir 34, the urine can flow back out the passageway 12 to the absorbent core 30, or can flow through the bodyside liner 14 directly to the absorbent core 30. This arrangement also allows for faster, more efficient absorption by the core 30 since urine is contacting a greater surface area of the core. The invention may also be arranged so that a portion of the reservoir is directly above the absorbent core 30. Such an arrangement requires that the containment flaps 10 be placed closer to one another than shown in the drawings.

Another embodiment of the invention is illustrated in FIG. 6. In this embodiment, the reservoir wall 16 is attached only to the containment flap 10. This arrangement may be more simply constructed than the earlier embodiments. A first surface of the upper edge 35 of reservoir wall 16 is sewn, bonded or otherwise attached near the distal edge 26 of the containment flap 10. The opposing surface of the lower edge 36 of the reservoir wall 16 is attached near the base 23 of the containment flap 10. While the opposing surface of the reservoir wall 16 is shown attached to the base of the flap in FIG. 6, either the same or the opposing surface of the reservoir wall 16 may provide the attachment which forms reservoir 34. Loci on the ends of the reservoir wall 16 are attached to the containment flap 10 to form a reservoir 34 sealed except for the passageways 12.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

Having thus described the invention, what is claimed is:

1. An absorbent article having a front portion, a rear portion and a crotch portion connecting said front and rear portions, said crotch portion having opposing longitudinal side portions, said absorbent article including a central portion extending along a length thereof said absorbent article comprising:

(a) an outer cover;

(b) a bodyside liner mounted to said outer cover, said bodyside liner and said outer cover, in combination, comprising a base structure of said absorbent article;

(c) an absorbent core located between said bodyside liner and said outer cover;

(d) first and second containment flaps joined to said bodyside liner, said first and second containment flaps being spaced from each other in the central portion of said absorbent article;

(e) first and second reservoir walls attached to the respective said containment flaps and, in combination with said containment flaps, forming respective first and second reservoirs disposed outwardly of said containment flaps; and (f) at least one passageway in each said containment flap for transferring exudates through the respective said containment flap and into the respective said reservoir.

2. An absorbent article according to claim 1 wherein said at least one passageway has a cross-sectional area corresponding to a diameter of between 5 millimeters and 25 millimeters.

3. An absorbent article according to claim 1 wherein said at least one passageway comprises a slit having a length between 5 millimeters and 25 millimeters.

4. An absorbent article according to claim 1, said first and second containment flaps comprising sections of a material severed by a serpentine cut forming corresponding serpentine edges along a length thereof, said serpentine edges forming lobes in said material, and corresponding spaces between said lobes, said spaces comprising said at least one passageway when said lobes of each said flap are attached to said base structure.

5. An absorbent article according to claim 1, said first and second containment flaps comprising sections of a material severed by a zig-zag cut forming corresponding zig-zag edges along a length thereof, said zig-zag edges forming teeth in said material, and corresponding spaces between said teeth, the spaces between said teeth comprising said at least one passageway when said teeth of each said flap are attached to said base structure.

6. An absorbent article according to claim 1 wherein said at least one passageway in each said containment flap comprises at least three passageways through each said containment flap.

7. An absorbent article according to claim 1 wherein said at least one passageway in each said containment flap is formed by slits in each said containment flap.

8. An absorbent article according to claim 1 wherein said first and second containment flaps are joined to said bodyside liner at intermittent locations, separated by spaces between adjacent ones of the intermittent locations, wherein said at least one passageway comprises a respective said space.

9. An absorbent article according to claim 1 wherein each said reservoir wall is attached to said bodyside liner of said absorbent article at a position disposed outwardly from the respective said containment flap.

10. An absorbent article according to claim 1 wherein said reservoir wall is attached to said outer cover of said absorbent article at a position disposed outwardly from said containment flap.

11. An absorbent article according to claim 1 wherein at least one passageway is disposed in the base of each said containment flap.

12. An absorbent article according to claim 1, said bodyside liner being positioned between said first and second containment flaps in the central portion of said absorbent article such that, in use, the body of the user is in direct contact with said bodyside liner in said central portion.

13. An absorbent article according to claim 1, said containment flaps each having a distal edge displaced from said bodyside liner when said absorbent article is in a relaxed condition, and a base edge joined to said bodyside liner adjacent a respective longitudinal edge of said absorbent core.

14. An absorbent article having a front portion and a rear portion, and a crotch portion connecting said front and rear portions, said crotch portion having opposing longitudinal side portions, said absorbent article comprising:

(a) an outer cover;

(b) a bodyside liner mounted to said outer cover, said bodyside liner and said outer cover, in combination, comprising a base structure of said absorbent article;

(c) an absorbent core located between said bodyside liner and said outer cover;

(d) first and second containment flaps, each said containment flap having a distal edge, and a base edge joined to said bodyside liner;

(e) first and second reservoir walls, attached to the corresponding said containment flaps near the distal edges of the corresponding said containment flaps and separately attached to the corresponding said containment flaps near the bases of the corresponding said containment flaps, and thereby forming corresponding first and second reservoirs between the respective said containment flaps and the respective said reservoir walls; and (f) at least one passageway in each said containment flap for transferring exudates through said containment flaps into said reservoirs.

15. An absorbent article according to claim 14 wherein said at least one passageway in each said containment flap has a cross-sectional area corresponding to a diameter of between 5 millimeters and 25 millimeters.

16. An absorbent article according to claim 14 wherein said at least one passageway in each said containment flap comprises a slit.

17. An absorbent article according to claim 14 wherein said at least one passageway in each said containment flap comprises at least three passageways through each said containment flap.

18. An absorbent article according to claim 14 wherein said at least one passageway in each said containment flap is formed by slits in the respective said flaps.

19. An absorbent article according to claim 14, including a central portion thereof extending along a length of said absorbent article, said first and second containment flaps being spaced from each other on opposing sides of said central portion.

20. An absorbent article according to claim 14, said bodyside liner being positioned between said first and second containment flaps such that, in use, the body of the user is in direct contact with said bodyside liner in said central portion.

21. An absorbent article according to claim 14, each said containment flap having a distal edge, and a base edge joined to said bodyside liner adjacent a respective longitudinal edge of said absorbent core.

22. An absorbent article having a front portion and a rear portion, and a crotch portion connecting said front and rear portions, said absorbent article having opposing outer longitudinal edges extending along a length thereof, said crotch portion having opposing longitudinal side portions, said absorbent article including a central portion extending along a length thereof, said absorbent article comprising:

(a) an outer cover;

(b) a bodyside liner mounted to said outer cover, said bodyside liner and said outer cover, in combination, comprising a base structure of said absorbent article;

(c) an absorbent core located between said bodyside liner and said outer cover, said absorbent core having opposing first and second side edges extending along the length of said absorbent article;

(d) first and second containment flaps, joined to said bodyside liner proximate respective said first and second side edges of said absorbent core, said bodyside liner being positioned between said first and second containment flaps such that, in use, the body of the user is in direct contact with said bodyside liner in said central portion;

(e) first and second reservoir walls, a first locus on each said reservoir wall being attached to a respective one of said containment flaps, a second locus on each said reservoir wall being attached to said base structure, said second locus being displaced from said first locus; the attachment of said reservoir walls to said base structure being disposed outwardly from the respective said containment flap and inwardly from the respective said outer longitudinal edge to form respective first and second reservoirs for exudates; and (f) at least one passageway in each said containment flap and extending into the respective said reservoir.

23. An absorbent article according to claim 22 wherein said at least one passageway in each said containment flap has a cross-sectional area corresponding to a diameter of between 5 millimeters and 25 millimeters.

24. An absorbent article according to claim 22 wherein said at least one passageway in each said containment flap comprises a slit.

25. An absorbent article according to claim 22, said first and second containment flaps comprising sections of a material severed by a serpentine cut forming corresponding serpentine edges along a length thereof, said serpentine edges forming lobes in said material, and corresponding spaces between said lobes, said spaces comprising said at least one passageway in each respective containment flap when said lobes of each said containment flap are attached to said bodyside liner.

26. An absorbent article according to claim 22, said first and second containment flaps comprising sections of a material severed by a zig-zag cut forming corresponding zig-zag edges along a length thereof, said zig-zag edges forming teeth in said material, and corresponding spaces between said teeth, the spaces between said teeth comprising said at least one passageway in each respective said containment flap when said teeth of each said containment flap are attached to said bodyside liner.

27. An absorbent article according to claim 22 including at least three passageways through each said containment flap.

28. An absorbent article according to claim 22 wherein said at least one passageway of each said containment flap is formed by slits in the respective said flaps.

29. An absorbent article according to claim 22 wherein said containment flaps are joined to said bodyside liner at intermittent locations, separated by spaces between adjacent ones of the intermittent locations, wherein said passageways comprise respective said spaces.

30. An absorbent article according to claim 22, each said containment flap having a distal edge, and a base edge joined to said bodyside liner adjacent a respective longitudinal edge of said absorbent core.

* * * * *